United States Patent
Lim et al.

(10) Patent No.: US 7,015,238 B2
(45) Date of Patent: Mar. 21, 2006

(54) CRYSTALLINE ORGANIC ACID SALT OF AMLODIPINE

(75) Inventors: Dong Kwon Lim, Seongnam (KR); Hyuk Koo Lee, Yongin (KR); Hea Ran Suh, Icheon (KR); Seong Hwan Cho, Suwon (KR); Kwang Hyeg Lee, Seongnam (KR); Yun Cheul Kim, Seoul (KR); Sung Hak Jung, Seoul (KR); Sung Hak Lee, Yongin (KR); Hyun Suk Kang, Seoul (KR); Kyung Mi Park, Seoul (KR); Yun Taek Jung, Seoul (KR); Jun Hee Cheon, Suwon (KR); Choong Sil Park, Icheon (KR); Yong Sik Youn, Yongin (KR); Young Hoon Kim, Seoul (KR); Kyu Jeong Yeon, Yongin (KR); Myeong Yun Chae, Seongnam (KR); Hae Tak Jin, Yongin (KR)

(73) Assignee: CJ Corp., (KR)

( * ) Notice: Subject to any disclaimer, the term of this patent is extended or adjusted under 35 U.S.C. 154(b) by 99 days.

(21) Appl. No.: 10/652,417

(22) Filed: Aug. 29, 2003

(65) Prior Publication Data

US 2004/0058967 A1    Mar. 25, 2004

(30) Foreign Application Priority Data

Sep. 19, 2002   (KR) ...................... 10-2002-0057328
Jul. 31, 2003   (KR) ...................... 10-2003-0053072

(51) Int. Cl.
*C07D 211/80*    (2006.01)
*A61K 31/47*     (2006.01)

(52) U.S. Cl. ..................... 514/356; 546/321
(58) Field of Classification Search ............... 546/322, 546/321; 514/356
See application file for complete search history.

(56) References Cited

U.S. PATENT DOCUMENTS

| 4,572,909 A | 2/1986 | Campbell et al. ........... 514/356 |
| 4,879,303 A | 11/1989 | Davison et al. ............. 514/356 |
| 6,291,490 B1 | 9/2001 | Young ....................... 514/356 |

FOREIGN PATENT DOCUMENTS

| CN | 1343663 A | 4/2002 |
| EP | 0 089 167 | 9/1983 |
| WO | WO 99/52873 | 10/1999 |
| WO | WO 02/053542 A1 | 7/2002 |

OTHER PUBLICATIONS

Database EPODOC 'Online!; European Patent Office, The Hague, NL; XP-002265143; *abstract * & CN1 343 663 A (Fu Junchang); Apr. 10, 2002.
European Search Report; Application No. 03019777.6-2101-; Date of Completion: Dec. 16, 2003: Dated: Jan. 13, 2004.

*Primary Examiner*—Zinna Northington Davis
(74) *Attorney, Agent, or Firm*—Cantor Colburn LLP

(57) ABSTRACT

A novel crystalline organic acid salt of amlodipine having improved physiochemical properties, a preparation method thereof and a pharmaceutical composition comprising the same are provided.

16 Claims, 2 Drawing Sheets

CRYSTALLINE ORGANIC ACID SALT OF AMLODIPINE

BACKGROUND OF THE INVENTION

1. Field of the Invention

The present invention relates to a novel organic acid salt of amlodipine (2-[(2-aminoethoxy)methyl]-4-(2-chlorophenyl)-1, 4-dihydro-6-methyl-3,5-pyridinedicarboxylic acid 3-ethyl 5-methyl ester), a preparation method thereof and a pharmaceutical composition comprising the same as an active ingredient.

2. Description of the Related Art

Amlodipine having a calcium channel blocking activity is useful in treating hypertension. As disclosed in EP 089 167, amlodipine is used in the form of salts formed with acids capable of forming non-toxic acid addition salts containing pharmaceutically acceptable anions, for example, hydrochloride, hydrobromide, sulphate, phosphate, acetate, maleate, fumarate, lactate, tartrate, citrate and gluconate salts. U.S. Pat. No. 6,291,490 discloses S-(−)-amlodipine that avoids the concomitant liability of adverse effects associated with the racemic mixture of amlodipine.

U.S. Pat. No. 4,879,303 discloses amlodipine besylate that satisfies the following physiochemical criteria: (1) good solubility; (2) good stability; (3) non-hygroscopicity; (4) processability for tablet formulation, etc.

However, amlodipine besylate has relatively low solubility at pH 1~7.4. Thus, there has been increasing demand for other salt forms for amlodipine having improved solubility. Also, amlodipine besylate, which is very unstable against light, has a problem in that it may produce various decomposed products.

Benzene sulfonic acid used in preparing amlodipine besylate is disadvantageously corrosive and noxious to be used for industrial purposes. Also, since benzene sulfonic acid is highly hygroscopic, it requires great care during transport and handling. Further, benzene sulfonic acid is unfavorably used in the form of dense oily material containing 90% of acid and 10% of water, as disclosed in WO 99/52873. To overcome these disadvantages, there has been proposed use of benzene sulfonic acids in the form of an ammonium salt. However, toxic ammonia gas generated during preparation of amlodipine besylate requires additional steps of absorbing and inactivating the toxic ammonia gas, which is also described in WO 99/52873.

SUMMARY OF THE INVENTION

The present invention provides a crystalline adipic acid salt of amlodipine. The crystalline adipic acid salt has superior physiochemical properties such as non-hygroscopicity, thermal stability, processability and photostability. Also, the adipic acid salt is industrially advantageous because it is free of corrosiveness and toxicity and is easy for handling due to its non-hygroscopicity, compared to benzene sulfonic acid used in preparing amlodipine besylate.

In accordance with an aspect of the present invention, there is provided a crystalline adipic acid salt of amlodipine.

In accordance with another aspect of the present invention, there is provided a method for preparing the crystalline adipic acid salt of amlodipine comprising reacting amlodipine with an adipic acid in an inert solvent.

In accordance with another aspect of the present invention, there is provided a pharmaceutical composition comprising the crystalline adipic acid salt of amlodipine as an active ingredient.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

The present invention provides a crystalline adipic acid salt of amlodipine represented by Formula 1:

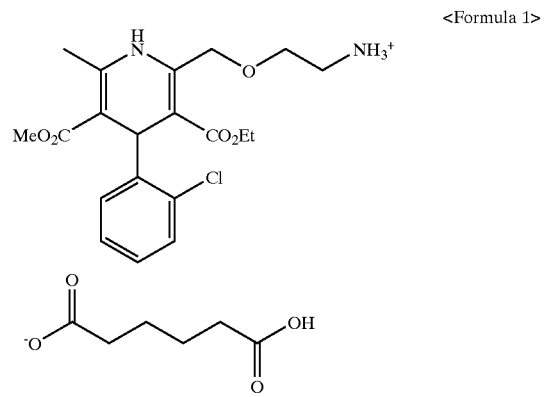

<Formula 1>

Figure 1:
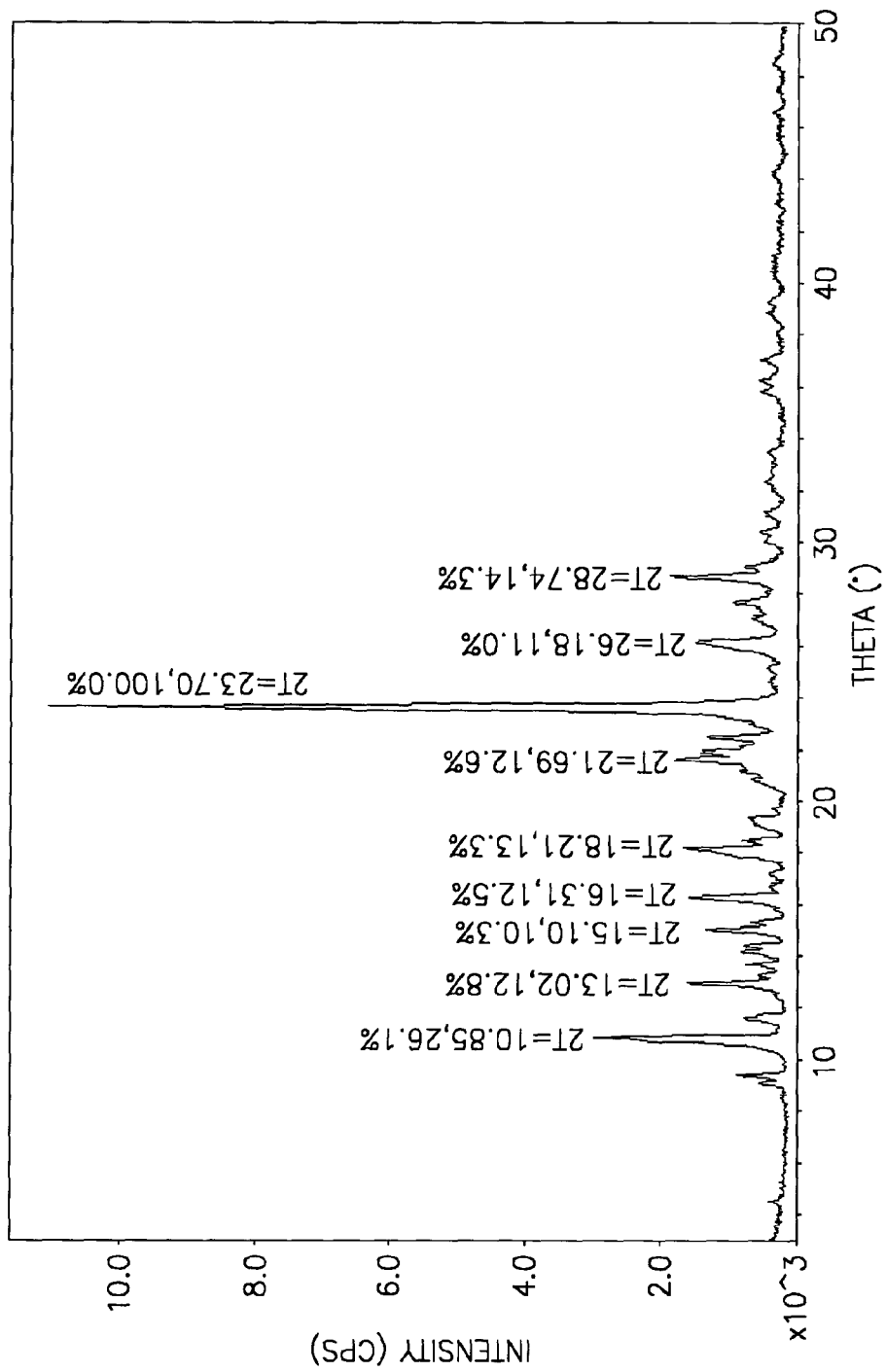
FIG. 1 shows the X-ray powder diffractogram for a crystalline adipic acid salt of amlodipine according to the present invention.

Measurement by an X-ray powder diffraction method revealed that the crystalline adipic acid salt of amlodipine preferably shows X-ray diffraction peaks at angles of at least 10.85°, 13.02°, 15.10°, 16.31°, 18.21°, 21.69°, 23.70°, 26.18°, and 28.74°. More preferably, the crystalline adipic acid salt of amlodipine according to the present invention has an X-ray powder diffraction pattern substantially as shown in FIG. 1.

The crystalline adipic acid salt of amlodipine according to the present invention preferably has a melting point from 164 to 168° C., as measured by a melting-point measurement method (1) described in "General Provisions of Preparations" of Korea Pharmacopoeia, 8th Ed., or by a capillary method described in European Pharmacopoeia, 4th Ed., in a temperature range of 50 to 200° C. with raising temperature at a rate of 1° C./min.

Compared to amlodipine besylate, the crystalline adipic acid salt of amlodipine according to the present invention has the equivalent or higher level of non-hygroscopicity, formulation processability and thermal stability and exhibits higher solubility at pH 1~8. In particular, the crystalline adipic acid salt of amlodipine according to the present invention has much higher photostability than other known organic acid salt forms, so that it can be used as a therapeutic agent for hypertension in a more photostable manner, which is required due to prolonged dosage.

The present invention provides an adipic acid salt of photostable amlodipine. The term "photostable" as used herein means that a material is resistant enough to maintain 90% or higher, preferably 95% or higher, more preferably 98% or higher, in its content, when exposed to light at 25° C. for a period of 4 weeks.

In one embodiment of the present invention, the crystalline adipic acid salt of amlodipine is prepared by reacting amlodipine with an adipic acid in an inert solvent. The following Reaction Scheme 1 illustrates the preparation process of the crystalline adipic acid salt of amlodipine.

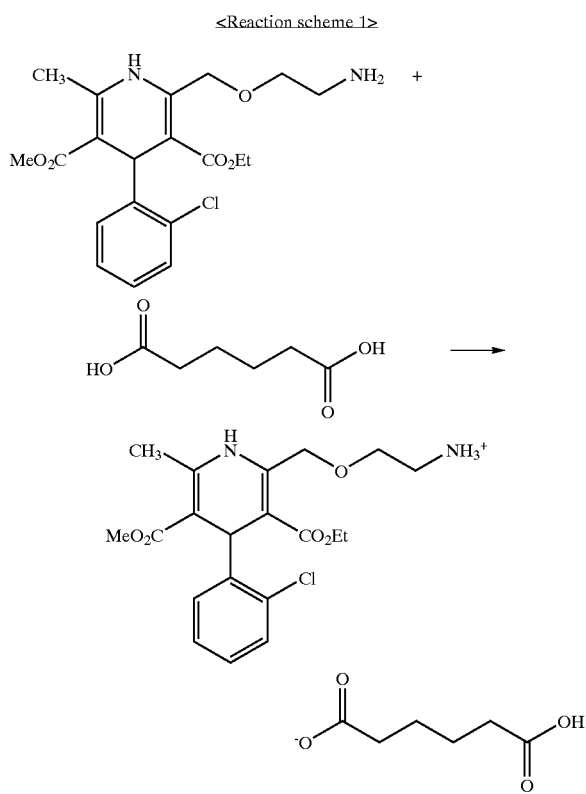

The adipic acid used in the present invention is used as food additives and is a stable, colorless solid. Since the adipic acid has no hygroscopicity, corrosiveness and toxicity, it can be safely manufactured and easily handled, so that it can be adaptively used for mass production of the crystalline adipic acid salt of amlodipine.

Examples of the inert solvent useful in the preparation method of the present invention include ethyl acetate, methanol, ethanol, isopropanol, acetonitrile, n-hexane, and isopropyl ether. Non-hygroscopicity of the product may very depending on the choice of the solvent. In the case of using methanol as the solvent, a superb product in view of non-hygroscopicity can be obtained. Thus, methanol is preferred because a crystalline product can be easily prepared.

The adipic acid is added dropwise in an amount of 1 to 2 equivalent, preferably 1.02 to 1.2 equivalent, based on 1 equivalent of amlodipine in an inert solvent, and the reaction is carried out at −5 to 30° C., preferably at 0 to 15° C., for 30 minutes to 5 hours, preferably for 1 to 3 hours.

The crystalline adipic acid salt of amlodipine can be prepared with high yield of 90% or higher according to the method of the present invention.

The present invention provides a pharmaceutical composition useful in treating ischaemic heart disease or hypertension, comprising the crystalline adipic acid salt of amlodipine in a therapeutically effective amount and a pharmaceutically acceptable diluent or carrier.

The composition according to the present invention can be formulated in the form of, but not limited to, oral dosage forms such as granules, powder, liquids, tablets, capsules or dry syrups, or parenteral dosage forms such as injections. In particular, tablets, capsules, liquids or injections are preferred.

The therapeutically effective amount of the crystalline adipic acid salt of amlodipine used in the composition according to the present invention is equivalent to the amount of amlodipine in the range of 2 to 10 mg per day, or in the range 3 to 16 mg per an unit dosage form.

As the pharmaceutically acceptable diluent or carrier, at least one selected from the group consisting of additives, disintegrants, binders and lubricants can be used in the composition according to the present invention. For example, when the composition according to the present invention is prepared in the form of solid formulations such as tablets or hard capsules, examples of the additive include microcrystalline cellulose, lactose, and low-substituted hydroxycellulose, and examples of the disintegrant include sodium starch glycolate, and anhydrous calcium hydrogen phosphate. Examples of the binder include polyvinylpyrrolidone, low-substituted hydroxypropylcellulose, and hydroxypropylcellulose. Examples of the lubricant include magnesium stearate, silicon dioxide, and talc.

Also, an excipient such as anhydrous dichloric calcium phosphate may be added to the tablets or a coating agent made of a water-insoluble material may be coated on the tablets for the purpose of preventing water from infiltrating into the tablets. Preferably, the coating agent has a dense molecular structure and is insoluble in an aqueous solution. Examples of the coating agent include polymers such as methacrylic acid copolymer, hydroxypropylmethyl cellulose phthalate, cellulose acetate phthalate, hydroxypropylmethyl cellulose acetate succinate, or polyvinyl alcohol. These polymers may be used for coating in individual form or in a mixture form. The coating agent may include excipients typically used in the art, for example, a plasticizer, an antiseptic, a coloring agent, or a light shielding agent.

The composition according to the present invention may be in the form of liquids such as a sterile aqueous solution, or injections. If necessary, the composition according to the present invention may comprise 10~40% propylene glycol, and sodium chloride in an amount sufficient to prevent hemolysis, e.g., approximately 1%.

The present invention will now be described in more detail through the following examples. The following examples are illustrative of the present invention, but are not meant to limit the scope of the invention.

EXAMPLES

Crystalline adipic acid salts of amlodipine were prepared according to the method according to the present invention and known amlodipine salts were prepared as Comparative Examples for evaluating various properties thereof. To test processability, the samples were formulated in the form of tablets, capsules and liquids. Also, various properties including hygroscopicity, solubility, thermal stability and photostability of the prepared crystalline adipic acid salts were compared with those of amlodipine besylate.

Comparative Example 1

Preparation of Amlodipine Besylate

Amlodipine was prepared by the method disclosed in U.S. Pat. No. 4,572,909 and amlodipine besylate was prepared by the method disclosed in U.S. Pat. No. 4,879,303.

Comparative Example 2

Preparation of Amlodipine p-Toluene Sulfonate 20 g of p-toluene sulfonic acid was dissolved in 100 ml of methanol, and 40 g of amlodipine prepared in Comparative Example 1 was dissolved in 500 ml of methanol and added dropwise to the solution of p-toluene sulfonic acid in methanol, followed by stirring at 23° C. for 3 hours. The resulting solid was filtered, washed with methanol (100 ml) and n-hexane (100 ml) and vacuum-dried.

Comparative Example 3

Preparation of Amlodipine Hydrochloride 12 ml of concentrated hydrochloride was dissolved in 100 ml of methanol, and 54 g of amlodipine prepared in Comparative Example 1 was dissolved in 500 ml of methanol and added dropwise to the solution of hydrochloride in methanol, followed by stirring at 23° C. for 3 hours. The resulting solid was filtered, washed with methanol (100 ml) and n-hexane (100 ml) and vacuum-dried.

Example 1

Preparation of Crystalline Adipic Acid Salt of Amlodipine 4.85 g (1.05 Eq.) of adipic acid was added to 10 ml of methanol in a 1L-three-neck flask, and a solution of amlodipine (13 g, 0.0316 mol) in 65 ml of methanol was added to the solution of adipic acid in methanol, followed by stirring at 23° C. for 2 hours. The reaction mixture was cooled to 7° C., stirred for one hour, and then filtered. The resulting solid was washed at 5° C. with 15 ml of methanol and 15 ml of acetone, filtered, and then vacuum-dried at 35° C. As a result, a white, crystalline adipic acid salt of amlodipine was obtained in an amount of 15.5 g (yield: 91%).

The results of elementary analysis for the obtained crystalline adipic acid salt of amlodipine are shown in Table 1.

TABLE 1

| Elemental analysis ($C_{26}H_{35}ClN_2O_8$) | | | | Unit (%) |
|---|---|---|---|---|
| Measured value | C: 55.9 | H: 6.4 | N: 5.1 | O: 24.1 |
| Calculated value | C: 56.3 | H: 6.4 | N: 5.1 | O: 26.0 |

Measurement was made in a temperature range of 50 to 200° C. with raising temperature at a rate of 1° C./min, using a melting-point measurement method (1) described in "General Provisions of Preparations" of Korea Pharmacopoeia, 8th Ed., or a capillary method described in European Pharmacopoeia, 4th Ed., and the melting-point of the crystalline adipic acid salt of amlodipine measured was 164 to 168° C.

Figure 2:
FIG. 2 shows the scanning electron microscope (SEM) photograph for the crystalline adipic acid salt of amlodipine according to the present invention.

The crystalline adipic acid salt of amlodipine was also subjected to X-ray powder diffraction, and the results are shown in FIG. 1, illustrating that it shows X-ray diffraction peaks at angles of 10.85°, 13.02°, 15.10°, 16.31°, 18.21°, 21.69°, 23.70°, 26.18°, and 28.74°. The SEM photograph of the crystalline adipic acid salt of amlodipine is shown in FIG. 2.

Example 2

Preparation of Tablets Comprising Crystalline Adipic Acid Salt of Amlodipine Tablets comprising the crystalline adipic acid salt of amlodipine were prepared by mixing ingredients as shown in Table 2.

TABLE 2

| Ingredient | Amount (mg/tablet) |
|---|---|
| Crystalline adipic acid salt of amlodipine | Equivalent to 5.0 mg of amlodipine |
| Low-substituted hydroxypropyl cellulose | 65 |
| Microcrystalline cellulose | 120 |
| Sodium starch glycolate | 4 |
| Magnesium stearate | 2 |

The respective ingredients were mixed and granulated with a roller compactor (supplied by Jowoon Machine Co., Korea), and resulting granules were punched into tablets by a tableting machine (supplied by Erweka Co, Germany).

Example 3

Preparation of Tablets Comprising Crystalline Adipic Acid Salt of Amlodipine Tablets comprising the crystalline adipic acid salt of amlodipine were prepared by mixing ingredients as shown in Table 3.

TABLE 3

| Ingredient | Amount (mg/tablet) |
|---|---|
| Crystalline adipic acid salt of amlodipine | Equivalent to 5 mg of amlodipine |
| Lactose | 180 |
| Crospovidone | 6 |
| Polyvinylpyrrolidone (K90) | 6 |
| Sodium starch glycolate | 4 |
| Magnesium stearate | 2 |

Using lactose, crospovidone and polyvinylpyrrolidone (K90), granule blends were prepared by a fluid bed equipment (Spir 'A' Flow model supplied by Freund Industrial Co., Ltd.) and the other ingredients were mixed and punched into tablets using a tableting machine (supplied by Erweka Co., Germany).

Example 4

Preparation of Capsules Comprising Crystalline Adipic Acid Salt of Amlodipine Capsules comprising the crystalline adipic acid salt of amlodipine were prepared by mixing ingredients as shown in Table 4.

TABLE 4

| Composition | Amount (mg/capsule) |
| --- | --- |
| Crystalline adipic acid salt of amlodipine | Equivalent to 5 mg of amlodipine |
| Low-substituted hydroxypropyl cellulose | 65 |
| Microcrystalline cellulose | 120 |
| Sodium starch glycolate | 4 |
| Magnesium stearate | 2 |

The respective ingredients were mixed and granulated using a roller compactor (supplied by Jowoon Machine Co., Korea), and resulting granules were filled into hard capsules using an encapsulating machine (supplied by Bosche Co.).

Example 5

Preparation of Capsules Comprising Crystalline Adipic Acid Salt of Amlodipine

Capsules comprising the crystalline adipic acid salt of amlodipine were prepared by mixing ingredients as shown in Table 5.

TABLE 5

| Ingredient | Amount (mg/capsule) |
| --- | --- |
| Crystalline adipic acid salt of amlodipine | Equivalent to 5 mg of amlodipine |
| Lactose | 180 |
| Crospovidone | 6 |
| Polyvinylpyrrolidone (K90) | 6 |
| Sodium starch glycolate | 4 |
| Magnesium stearate | 2 |

Using lactose, crospovidone and polyvinylpyrrolidone (K90), granule blends were prepared by a fluid bed equipment (Spir 'A' Flow model), and the other ingredients were mixed and filled into the hard capsules using an encapsulating machine (supplied by Bosche Co.).

Example 6

Evaluation of Hygroscopicity of Crystalline Adipic Acid Salt of Amlodipine

Water contents (by percent (%) measured by Karl Fisher method) of the crystalline adipic acid salt of amlodipine prepared in Example 1 and amlodipine besylate prepared in Comparative Example 1 were measured under various humidity conditions at 25° C., and the measurement results are shown in Table 6.

TABLE 6

| Storage conditions (Relative humidity) | | 25% | 60% | 75% | 95% |
| --- | --- | --- | --- | --- | --- |
| Storage period | Initial stage | 1 week | 1 week | 1 week | 1 week |
| Adipic acid salt | 0.10% | 0.10% | 0.10% | 0.14% | 0.16% |
| Besylate salt | 0.14% | 0.10% | 0.09% | 0.15% | 0.17% |

As shown in Table 6, the non-hygroscopicity of the crystalline adipic acid salt of amlodipine was the equivalent to or higher than that of amlodipine besylate at various levels of relative humidity. The hygroscopicity levels of the samples were much less than 0.5% at 95% of relative humidity, suggesting that the samples can be advantageously used as salts for various types of formations such as tablets, capsules or injections.

Example 7

Evaluation of Solubility of Crystalline Adipic Acid Salt of Amlodipine

Solubilities of the crystalline adipic acid salt of amlodipine prepared in Example 1 and amlodipine besylate prepared in Comparative Example 1 were measured at 25° C. at various pHs, and the results are shown in Table 7, in which the solubilities were converted into the corresponding solubilities of amlodipine (mg/ml).

TABLE 7

| | Salt used | | |
| --- | --- | --- | --- |
| Solvent | Adipic acid salt (mg/ml) | Besylate (mg/ml) | |
| Distilled water | 1.53 | 1.29 | |
| PH 2.0 | 3.68 | 1.29 | Dissolved in |
| PH 4.0 | 2.27 | 1.32 | buffered solution |
| PH 6.0 | 2.30 | 1.28 | with 0.2 of ionic |
| PH 7.0 | 4.48 | 0.64 | strength at 25° C. |
| PH 7.4 | 2.79 | 1.35 | |
| PH 8.0 | 2.35 | 1.25 | |

As shown in Table 7, when dissolved in distilled water and buffered solutions with various pHs, the crystalline adipic acid salt of amlodipine has solubility of approximately two times higher than amlodipine besylate at all pHs, except for the case of using the distilled water. Thus, enhanced bioavailability of the crystalline adipic acid salt of amlodipine according to the present invention is expected.

Example 8

Evaluation of Stability of Crystalline Adipic Acid Salt of Amlodipine

1. Thermal Stability of Crystalline Adipic Acid Salt of Amlodipine in a Solid State The crystalline adipic acid salt of amlodipine prepared in Example 1 and amlodipine besylate were subjected to an acceleration test at 60° C., and the results are shown in Table 8. The amlodipine besylate used as a sample for comparison was prepared according to Comparative Example 1.

TABLE 8

| | Initial stage | 1 week | 2 weeks | 4 weeks |
| --- | --- | --- | --- | --- |
| Adipic acid salt | 99.8% | 99.8% | 99.7% | 99.7% |
| Besylate | 99.6% | 99.6% | 99.5% | 99.5% |

(Unit: %, HPLC)

High Performance Liquid Chromatography (HPLC) analysis was conducted under the following conditions:

Detector: UV absorption (237 nm)

Column: Octadesyl silica gel C18 (4.6 mm×150 mm, 5 μm)

Mobile phase: Potassium dihydrogen phosphate monobasic (0.03 M): Methanol=4:6 (by volume)

Flow rate: 1.5 ml/min

As shown in Table 8, both the crystalline adipic acid salt of amlodipine and amlodipine besylate exhibited little change in the content in the acceleration test conducted at 60° C., suggesting that the adipic acid salt amlodipine and amlodipine besylate have good thermal stability.

2. Stability of Crystalline Adipic Acid Salt of Amlodipine in a Liquid State

To evaluate the stability of samples in a liquid state, the crystalline adipic acid salt of amlodipine prepared in Example 1 and amlodipine besylate prepared in Comparative Example 1 were dissolved in distilled water and stored for 4 weeks at 25° C., protected from light for observation of a change in the content. The observation was made under the same conditions as in the HPLC analysis for evaluating the thermal stability of samples in a solid state.

The stability test revealed that both the crystalline adipic acid salt of amlodipine and amlodipine besylate produced no decomposed products. Also, no significant changes in the content were observed in both the crystalline adipic acid salt of amlodipine and amlodipine besylate.

Example 9

Evaluation of Photostability of Crystalline Adipic Acid Salt of Amlodipin

To evaluate photostability, the crystalline adipic acid salt of amlodipine prepared in Example 1 and other salt forms prepared in Comparative Examples 1 through 3 were used. The samples were stored for 4 weeks while being exposed to sunlight at 25° C., and the results are shown in Table 9.

TABLE 9

| | Initial stage Content (HPLC) | Stored at 25° C. for 4 weeks with light exposure Content (HPLC) |
|---|---|---|
| Adipic acid salt | 99.5% | 99.1% |
| Besylate salt | 99.2% | 82.5% |
| Tosylate salt | 99.2% | 72.0% |
| Hydrochloride salt | 99.0% | 60.5% |

As shown in Table 9, while the surface of amlodipine besylate exposed to light turned yellow while it was white at an initial stage, the crystalline adipic acid salt of amlodipine remained white even after it was exposed to light. To evaluate photostability, a change in the content (%, HPLC) of each sample was observed under the same HPLC analysis conditions as in the evaluation of thermal stability. Photostability is quite an important factor in therapeutic agents for treating hypertension because they are administered to patients over a prolonged period of dosage. The evaluation results showed that the crystalline adipic acid salt of amlodipine had better photostability than amlodipine besylate.

The crystalline adipic acid salt of amlodipine according to the present invention has good physiochemical properties, including non-hygroscopicity, stability, solubility, and processability. In particular, the crystalline adipic acid salt of amlodipine according to the present invention has superb photostability. Thus, the crystalline adipic acid salt of amlodipine according to the present invention can be easily carried by a patient and stored for an extended period. Also, since adipic acid used in preparing the crystalline adipic acid salt of amlodipine is neither corrosive nor noxious, and is easy for handling due to its non-hygroscopicity, it can be advantageously used for industrial purposes.

What is claimed is:

1. A crystalline adipic acid salt of amlodipine, wherein, as measured by X-ray powder diffraction, the crystalline adipic acid salt has X-ray diffraction peaks at angles of at least 10.85°, 13.02°, 15.10°, 16.31°, 18.21°, 21.69°, 23.70°, 26.18°, and 28.74°.

2. The crystalline adipic acid salt of amlodipine of claim 1, having an X-ray powder diffraction pattern substantially same as shown in FIG. 1.

3. The crystalline adipic acid salt of amlodipine of claim 1, having a melting point of 164 to 168° C.

4. The crystalline adipic acid salt of amlodipine of claim 1, wherein the crystalline adipic acid salt is photostable.

5. A method for preparing a crystalline adipic acid salt of amlodipine, comprising:
reacting amlodipine with an adipic acid in methanol,
wherein, as measured by X-ray powder diffraction, the crystalline adipic acid salt has X-ray diffraction peaks at angles of at least 10.85°, 13.02°, 15.10°, 16.31°, 18.21°, 21.69°, 23.70°, 26.18°, and 28.74°.

6. The method of claim 5, wherein the crystalline adipic acid salt of amlodipine has an X-ray powder diffraction pattern substantially same as shown in FIG. 1.

7. The method of claim 5, wherein the crystalline adipic acid salt of amlodipine has a melting point of 164 to 168° C.

8. The method of claim 5, wherein the crystalline adipic acid salt of amlodipine is photostable.

9. A pharmaceutical composition for treating ischaemic heart disease or hypertension, comprising the crystalline adipic acid salt of amlodipine claimed in claim 1 in a therapeutically effective amount and a pharmaceutically acceptable diluent or carrier.

10. The pharmaceutical composition of claim 9, wherein the pharmaceutical composition is in the form of tablets or capsules.

11. The pharmaceutical composition of claim 9, wherein the pharmaceutical composition is in the form of liquids or injections.

12. The pharmaceutical composition of claim 9, wherein the crystalline adipic acid salt of amlodipine has an X-ray powder diffraction pattern substantially same as shown in FIG. 1.

13. The pharmaceutical composition of claim 9, wherein the crystalline adipic acid salt of amlodipine has a melting paint of 164 to 168° C.

14. The pharmaceutical composition of claim 9, wherein the crystalline adipic acid salt of amlodipine is photostable.

15. The pharmaceutical composition of claim 9, wherein the therapeutically effective amount of the crystalline adipic acid salt of amlodipine has an amount of 2 to 10 milligrams per day.

16. The pharmaceutical composition of claim 9, wherein the therapeutically effective amount of the crystalline adipic acid salt of amlodipine has an amount of 3 to 16 milligrams per an unit dosage form.

* * * * *